(12) United States Patent
Shekalim

(10) Patent No.: US 6,679,865 B2
(45) Date of Patent: Jan. 20, 2004

(54) FLUID FLOW METER FOR GRAVITY FED INTRAVENOUS FLUID DELIVERY SYSTEMS

(75) Inventor: Avraham Shekalim, Nesher (IL)

(73) Assignee: Nedrip Ltd., Migdal Haemek (IL)

( * ) Notice: Subject to any disclaimer, the term of this patent is extended or adjusted under 35 U.S.C. 154(b) by 200 days.

(21) Appl. No.: 10/004,855

(22) Filed: Dec. 7, 2001

(65) Prior Publication Data

US 2003/0109836 A1 Jun. 12, 2003

(51) Int. Cl.$^7$ .............................. A61M 5/00; A61M 5/14
(52) U.S. Cl. .................... 604/253; 604/246; 604/30; 604/65
(58) Field of Search .................... 604/246, 251, 604/252, 253, 325, 27, 30, 31, 65, 67, 207; D24/108

(56) References Cited

U.S. PATENT DOCUMENTS

| | | |
|---|---|---|
| 4,207,871 A | 6/1980 | Jenkins |
| 4,559,044 A | 12/1985 | Robinson et al. |
| 6,176,845 B1 * | 1/2001 | Kriesel et al. ............... 604/132 |
| 6,236,624 B1 * | 5/2001 | Kriesel et al. ............... 368/65 |
| 6,254,576 B1 | 7/2001 | Shekalim |
| 6,270,483 B1 * | 8/2001 | Yamada et al. ............. 604/249 |
| 6,554,805 B2 * | 4/2003 | Hiejima ....................... 604/247 |

* cited by examiner

Primary Examiner—Brian L. Casler
Assistant Examiner—Jennifer Maynard
(74) Attorney, Agent, or Firm—Mark M. Friedman

(57) ABSTRACT

The present invention is a flow metering system for accurately metering and regulating the flow rate of fluid in a gravity fed intravenous fluid delivery system. The fluid flow is directed through a flow path guide that is suspended at an angle from one end. As the fluid flows through the flow path guide, the flow path guide bends due to the weight of the fluid. A drop of fluid forms at the end of the flow path guide then falls off, thereby releasing the flow path guide, which springs back it its original position. The sequence of drops and springing back continues throughout the fluid delivery procedure, and is monitored by sensors. The resultant data is used by a processor to determine the flow rate of the fluid. The flow rate may be adjusted as needed by a flow regulator that is responsive to an adjustment actuator that is controlled by the processor.

25 Claims, 6 Drawing Sheets

FLUID FLOW METER FOR GRAVITY FED INTRAVENOUS FLUID DELIVERY SYSTEMS

FIELD AND BACKGROUND OF THE INVENTION

The present invention relates to gravity fed intravenous delivery systems and, in particular, it concerns a system for metering and regulating the fluid flow thereof.

A typical gravity fed intravenous system may be as simple as an IV bag hanging on a pole and a medical staff person manually adjusting a valve to limit the flow rate, but not control it accurately. Traditionally, the flow rate of the fluid from the IV bag was roughly measured with a drip chamber at the IV bag and controlled by a clamp varying the restriction in a delivery line extending between the drip chamber and the patient. A medical staff person visually counts the drop rate in the drip chamber and manually sets the clamping or pinching device to achieve a desired flow rate. The accuracy of this system assumes the consistency in volume of each drop of fluid into the drip chamber. However, the drop size is dependent on the orifice diameter, the inner and the outer diameter of the tip in the drip chamber, which varies within a manufacturing tolerance for a particular container. Even the nominal orifice diameter is not uniform throughout the industry. Manufacturers sell drip chambers having 10, 15, 20 and 60 drop per milliliter chambers, for example. In addition, the volume of the drops may vary with temperature, viscosity and rate. Further, the rate remains essentially constant as long as the head of liquid does not change appreciably. Of course, as the liquid is being fed to the patient, the pressure head slowly decreases causing the flow rate to decrease proportionately, and if a precise amount of liquid is to be supplied to the patient, this change must be taken into account when the valve is initially set, or in the alternative, the manual valve can be reset from time to time. However, should the patient roll over or make some other movement, which appreciably changes the vertical distance between the IV bag and the catheter, the flow rate changes more dramatically.

There have been numerous proposals in prior art for devices that do not rely on gravity as the driving force for the flow of fluid through the system. These systems include the use of pump devices or devices that apply pressure directly to the IV bag in order to create and maintain a predefined head pressure. The pressurized fluid is then regulated. This group is characterized by various styles of peristaltic-type infusion pumps, which manipulate the fluid flow in the delivery line. There a several problems associated with these non-gravity fed devices. They provide fluid medication to the patient at high pressure this may result in physical damage to the vein or artery of the patient. With pressurization comes the chance of bubbles in the system, and these devices must include bubble detectors. Their complexity of design results in complex operation that may increase the opportunity for malfunction and the need for enough energy to power the device. The need for energy usually requires that the device be plugged into a wall outlet, there by restricting the mobility of the patient while receiving treatment. Further, the intricacy of manufacture results in high purchase costs to the consumer, i.e. hospitals and clinics, which generally have tight and limited budgets. Therefore, these devices are available in relatively limited quantities and used on a "most needed case" basis.

The devices of U.S. Pat. No. 4,207,871 to Jenkins and U.S. Pat. No. 4,559,044 to Robinson, et al. are attempts to utilize relatively small pumps. These are still active pumps and suffer from all of problems enumerated above.

Returning now to gravity fed systems. As mentioned above, the most common way of metering the fluid flow in a gravity fed intravenous system is for a medical staff person to manually count drops, readjusting a flow adjustment valve as needed throughout the fluid delivery process. One attempted method to overcome the obvious problems of this manner of flow metering has been by the use of optical drop counters. While this provides a means of substantially constant monitoring not available from human staff, the problems of drop size and fluid viscosity still exist since this is still just counting the drops.

There is therefore a need for a low cost fluid flow meter for use with gravity fed intravenous fluid delivery systems that is unaffected by the properties of the intravenous system to which it is attached, i.e. changing head pressure, that is accurate regardless of any physical properties of a particular fluid, i.e. viscosity, and specific density, and that is able to adjust the flow rate as necessary to maintain a prescribed flow rate. It would be preferable that the components of the system that come in contact with the fluid be made disposable.

SUMMARY OF THE INVENTION

The present invention is a flow metering system for accurately metering and regulating the flow rate of fluid in a gravity fed intravenous fluid delivery system.

According to the teachings of the present invention there is provided, a flow meter for achieving an accurate reading of the flow rate of a fluid, the flow meter comprising: a) a fluid flow path guide along which the fluid flows, the flow path guide being deployed at an angle with an upper end fixedly attached to a meter inlet and a lower end suspended above a reservoir attached to a meter outlet, the flow path guide having an initial position, the flow path guide configured so as to have a given elastic resiliency such that when bent and subsequently released the flow path guide returns to the initial position; b) a sensing device configured and deployed so as to generate an output which varies as a function of movements of the flow path guide; and c) a processing unit in electronic communication with the sensing device, the processing unit configured to use the output from the sensing device to determine the flow rate.

According to a further teaching of the present invention, the given elastic resiliency is inherent to the configuration of the flow path guide.

According to a further teaching of the present invention, the flow path guide includes a conduit that is substantially closed along a dimension called length, the conduit being open to fluid flow at each of two ends.

According to a further teaching of the present invention, the flow path guide includes a helical spring.

According to a further teaching of the present invention, the given elastic resiliency is inherent to a material from which the flow path guide is fabricated.

According to a further teaching of the present invention, the given elastic resiliency is inherent to a material from which an element, to which the flow path guide is attached, is fabricated.

According to a further teaching of the present invention, the sensing device includes at least one magnetic sensor.

According to a further teaching of the present invention, the sensing device includes an optical sensor.

According to a further teaching of the present invention, at least one property that enables the sensing device to discern the movements of the flow path guide is inherent to a material from which the flow path guide is fabricated.

According to a further teaching of the present invention, at least one property that enables the sensing device to discern the movements of the flow path guide is inherent to a material that is affixed to the flow path guide.

According to a further teaching of the present invention, the flow path guide, the sensing device and the processor are housed in a single housing.

According to a further teaching of the present invention, the flow path guide is deployed within a housing, the housing including the meter inlet and the meter outlet, and the sensing device and the processor are removably interconnected with the housing.

There is also provided according to the teachings of the present invention, a flow metering system for accurately metering and regulating the flow rate of fluid flowing through a tube of a fluid delivery system, the flow metering system comprising: a) an adjustable flow regulator assembly having a regulator inlet, the flow regulator thereby receiving a flow of fluid, the flow regulator being configured so as to regulate the flow of fluid through the regulator, the regulator including an adjustment mechanism responsive to an adjustment actuator, the flow regulator further having a regulator outlet; and b) the flow meter of claim 1 in fluid communication with the regulator; wherein the adjustment actuator is in electronic communication with, and responsive to, the processing unit, so as to regulate the flow.

According to a further teaching of the present invention, the fluid delivery system includes a gravity fed intravenous fluid delivery system for delivery of fluid drugs to a patient.

According to a further teaching of the present invention, the flow regulator assembly includes a variable length elongated flow path.

According to a further teaching of the present invention, the adjustment mechanism is configured so as to vary length of the elongated flow path.

According to a further teaching of the present invention, the processing unit, and the adjustment actuator are included in a base housing unit.

According to a further teaching of the present invention, at least part of the flow regulator and at least part of the flow meter are included in a removable fluid flow path unit.

There is also provided according to the teachings of the present invention, a flow metering method for accurately metering the flow rate of fluid flowing through a tube of a fluid delivery system, the flow metering method comprising: a) directing the flow along a fluid flow path guide, the flow path guide being deployed at an angle with an upper end fixedly attached to a meter inlet and a lower end suspended above a reservoir attached to a meter outlet, the flow path guide having an initial position, the flow path guide configured so as to have a given elastic resiliency such that when bent and subsequently released the flow path guide returns to the initial position, the bending being caused by weight from a build up of fluid at a lower end and the return of the flow path guide to the initial position occurring when a drop is released from the lower end of the flow path guide; b) sensing movements of the flow path guide; and c) processing output resulting from the sensing, so as to derive fluid flow rate.

According to a further teaching of the present invention, the flow is regulated based on the processing.

According to a further teaching of the present invention, the regulating is accomplished by varying the length of a variable length elongated flow path.

According to a further teaching of the present invention, the varying is accomplished by activation of an adjustment actuator.

According to a further teaching of the present invention, the activation includes activation of an electric-motor-driven gear assembly.

According to a further teaching of the present invention, the regulation maintains a predetermined flow rate.

According to a further teaching of the present invention, the regulation changes the flow rate according to a predefined program.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a flow metering system for accurately metering and regulating the flow rate of fluid in a gravity fed intravenous fluid delivery system.

The principles and operation of a flow metering system according to the present invention may be better understood with reference to the drawings and the accompanying description.

Before turning to details of the present invention, it should be appreciated that the present invention provides a flow meter that is preferably configured for use in conjunction with the flow regulator of U.S. Pat. No. 6,254,576 (as in the preferred embodiment discussed here). However, the flow meter may be configured to be individually combined with other corresponding components, or for use as a stand-alone device. The flow meter will be discussed in FIGS. 2–4. The flow regulator, and control thereof, will be discussed in FIGS. 5 and 6. It should be note here that while in the following discussion the flow meter is deployed down stream from the flow regulator, this deployment arrangement is neither required nor preferred.

Figure 1:
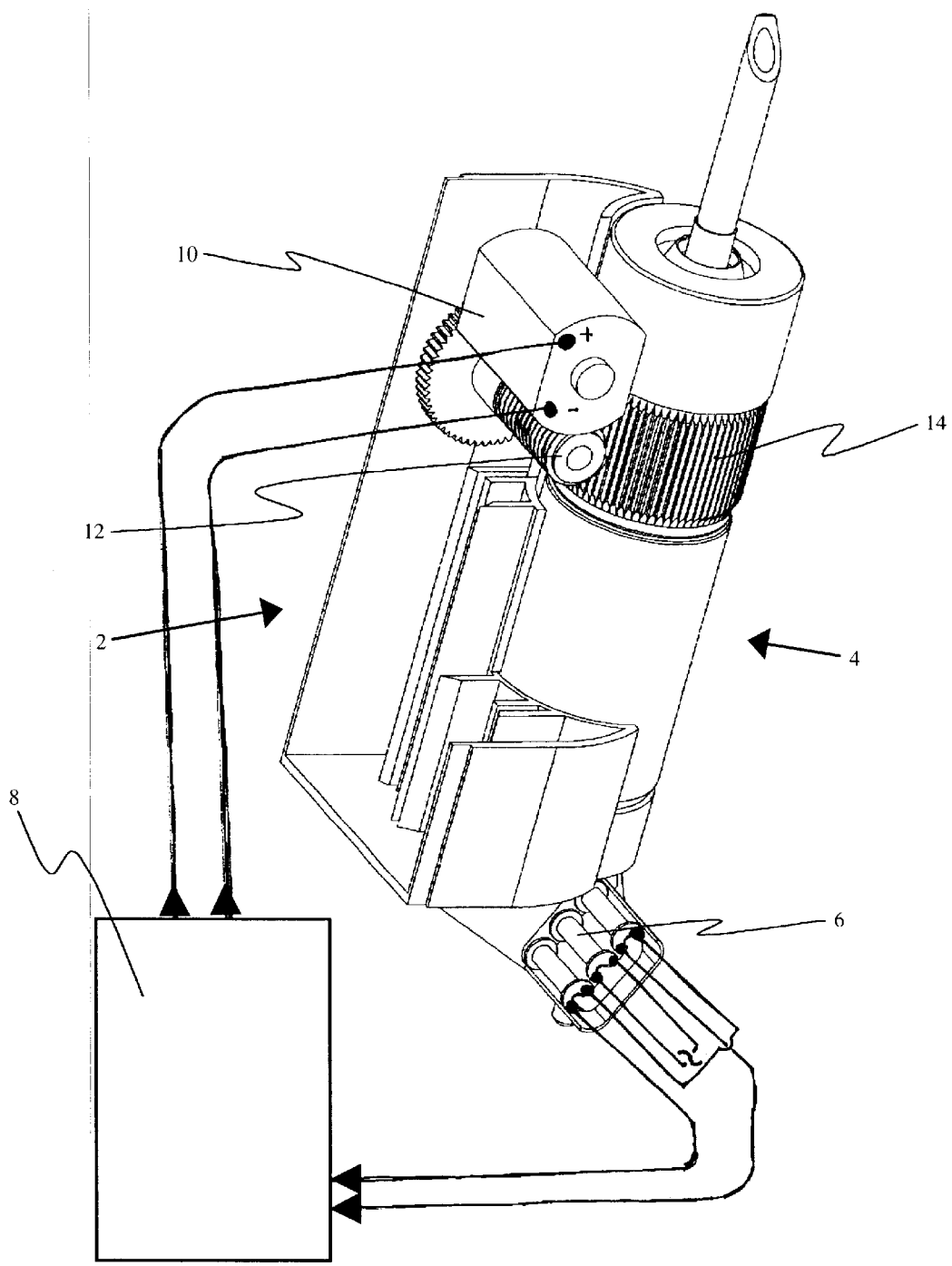
FIG. 1 is an isometric view of a flow metering system constructed and operative according to the teachings of the present invention, together with an electrical schematic of this preferred embodiment.

Referring now to the drawings, FIG. 1 provides an overview of a preferred embodiment of the present invention that will be the focus of this non-limiting discussion. This preferred embodiment consists of two separable units, a base unit 2 and a detachable canister unit 4. Housed in the canister unit are a flow meter, which is not visible in this view, that is located adjacent to the sensing device 6, which is also housed in the canister unit along with a flow regulator that has an exterior adjustment configuration consisting of a worm wheel 14 located on the outer surface of the housing.

Housed in the base unit are a processing unit 8, and an adjustment actuator 10 consisting of a motor driven worm gear 12.

A brief explanation, which will be expanded below, of the operation of the preferred embodiment of the present invention shown here is as follows. As the fluid flows through the flow meter, the movements of a flow path guide located in the flow meter are detected by the sensing device. This process is discussed further in FIG. 2. The processing unit 8 uses output form the sensing device 6 to determine the flow rate of the fluid and activates the adjustment actuator 10 accordingly. When activated, the motor driven worm gear 12 of the adjustment actuator is rotated. As the worm gear rotates, the worm wheel 14, in turn, is rotated causing the adjustment mechanism to also rotate. This rotation adjusts the regulation of the flow of fluid through the system.

Figure 2:
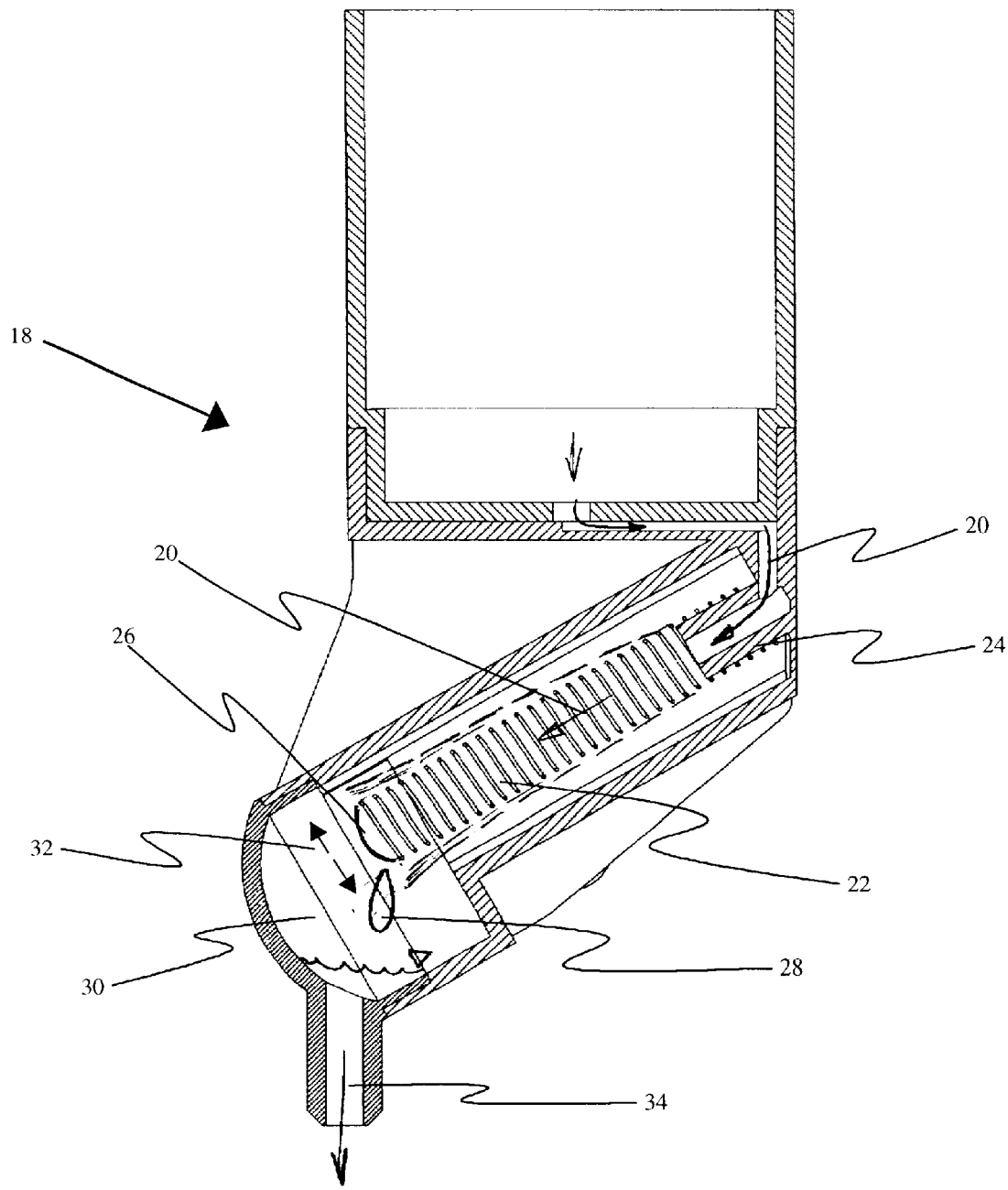
FIG. 2 is a cut-away side view of the preferred embodiment of the flow meter constructed and operative according to the teachings of the present invention.

Turning now to a detailed look at the components of the present invention as they are shown in this preferred embodiment, FIG. 2 shows the flow path 20 of the fluid through the flow meter. A flow path guide 22 is suspended at an angle in the meter housing 18 by attachment to the housing at a connection extension 24. The term "flow path guide", as used herein, refers to an element along whose length the fluid flow is directed. The element has properties of elastic resiliency such that when bent and subsequently released will return to its original position and directs the flow of the fluid along the length of the flow path guide. The flow path guide may be configured as a "conduit", that is, enclosed along its length, however, it need not be completely closed as long as the surface tension of the fluid is sufficient to keep the liquid flowing along the flow path guide. The flow path guide shown here is configured as a metallic helical spring 22. As the fluid flows along the flow path guide, the flow path guide bends due to the added weight of the fluid. The fluid collects at the lower end of the flow path guide, which continues to bend further under the added weight, while a drop 26 forms. As shown here, by non-limiting example, when the drop falls off 28, the flow path guide "springs" back to its original position by undergoing a series of reciprocating movements 32. The drop falls into the reservoir 30, and the fluid flows out of the meter through outlet 34. This pattern of drops bending and releasing the flow path guide continues throughout the fluid delivery procedure. Depending on the elastic properties of the material from which the flow path guide is fabricated the flow path guide may return to its original position with or without undergoing the series of reciprocating movements mentioned above. It should be noted that the flow path guide may be configured from materials with inherent elastic properties or it may be attached to at least one member with the requisite elastic properties.

Figure 3:
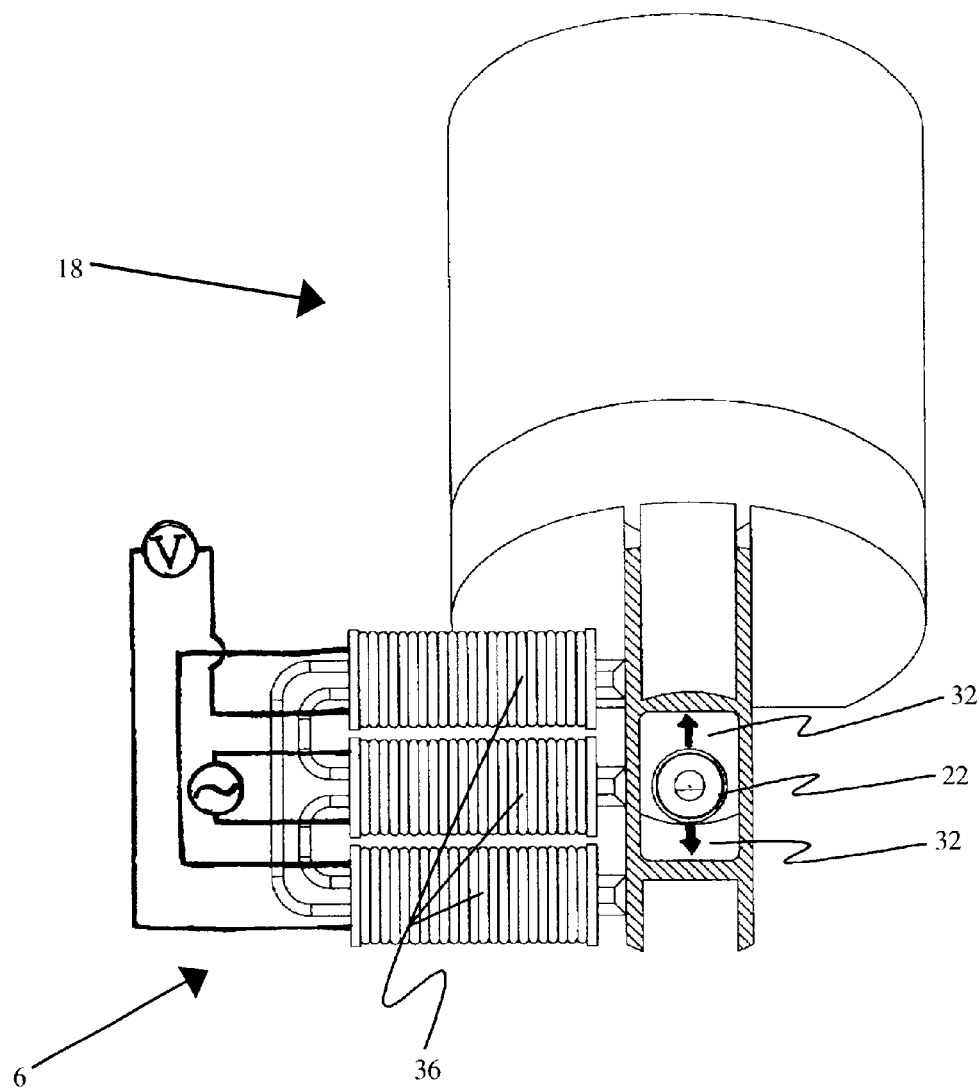
FIG. 3 is a cut-away front view of the preferred embodiment of the flow meter of FIG. 2.

The deployment of the sensing device 6, shown in FIG. 3 as a linear variable differential transformer, herein referred to as LVDT, magnetic sensor, is such that the movement of the flow path guide may be monitored. Here, by non-limiting example, the magnetic fields of the sensors 36 are altered by the movements 32 of the flow path guide 22. These alterations indicate the movement of the flow path guide, such as bending, and possible remaining substantially motionless in a terminally bent position, while a drop is forming and the sudden gross "springing" movement when the drop falls off the flow path guide, followed by sequentially smaller reciprocating movements if they occur, until the weight of fluid for another drop brings the spring back to the terminally bent position. In the simplest terms, the processor uses the interval between the sudden gross movements, together with the amount of movement of the flow path guide to determine the weight of each drop and thereby calculating the flow rate based on drops per minute, or other suitable time interval. That is to say, if the rate of the drops and the weight necessary to bend the flow path guide to the point where a drop falls off are known the rate of medication delivery may be calculated. However, the elastic resiliency of some materials may include a natural reciprocating frequency that when coupled with the drip frequency, creates a near harmonic resonance which may affect the movement of the flow path guide. Any harmonic resonance needs to be determined and taken into consideration when calculating the flow rate of the fluid. The natural reciprocating frequency of the flow path guide may also be affected by the viscosity and the specific gravity of the fluid medication. All of these factors may possibly be use by the processing unit to accurately determine the delivery rate of the fluid medication to the patient. It should be noted that the flow path guide may be configured from materials with inherent magnetic properties or from materials with added magnetic properties, either as alloys or as attachments. The sensing device may employ, but not be limited to, magnetic such as LVDT (as mentioned), capacitative or optical sensors. If optical sensors are employed, the flow path guide need not possess the magnetic properties discussed earlier.

Figure 4:
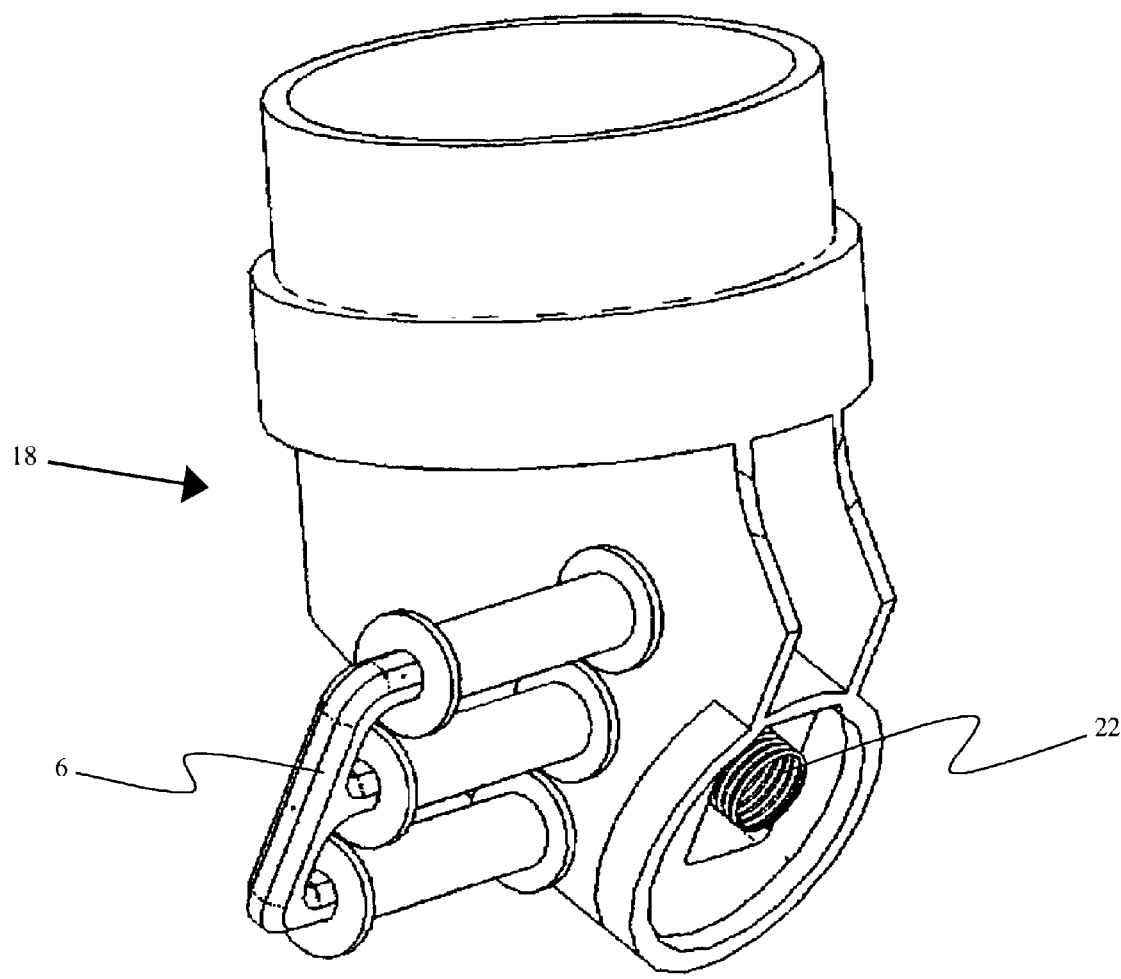
FIG. 4 is an isometric view of the flow meter of FIG. 2.

FIG. 4 provides an isometric view of the meter housing 18, showing the deployment relationship of the sensing device 6 to the flow path guide 22. It should be noted that the sensing device may be included in the base unit. Further, the sensing device may be fixedly or removably attached to the components of the system with which the sensing device is associated.

Figure 5:
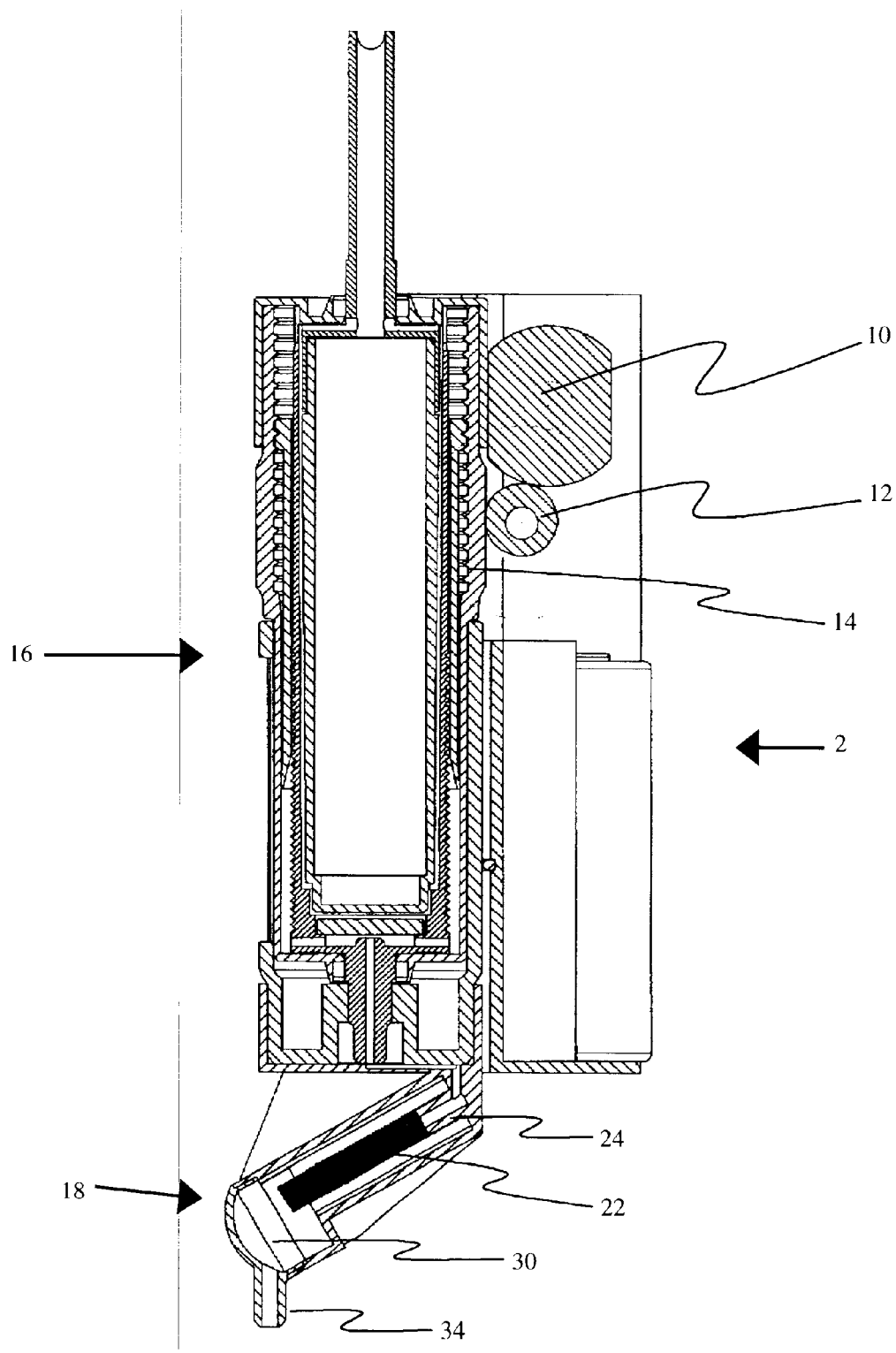
FIG. 5 is a cut-away side view of the preferred embodiment of the flow metering system of FIG. 1.

FIG. 5 is a cut-away side view of the system of FIG. 1. Here, the flow meter 18 and the flow regulator 16 are easily discernible. The other elements shown have been discussed previously and are numbered here for reference purposes. It should be noted here, as will be appreciated by one ordinarily skilled in the art, that the teachings of the present invention allow for a variety of implementations and embodiments. By non-limiting example: the entire flow metering system may be configured in a single housing; or the flow meter and the flow regulator may be configured as totally separate units, which may be deployed together or with other corresponding units.

Figure 6:
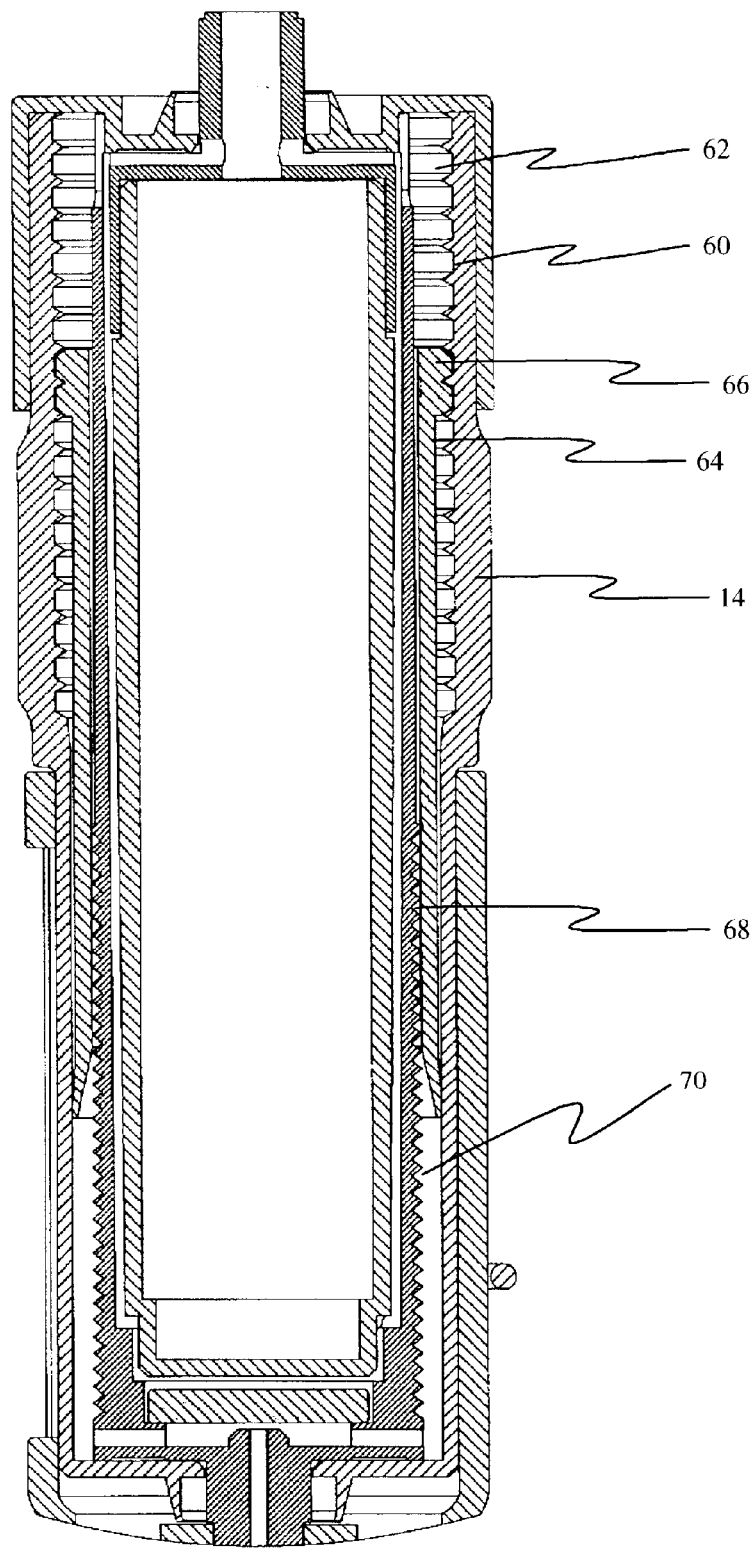
FIG. 6 is a cut-away side view of a flow regulator constructed and operative according to the teachings of the present invention.

Turning now to a preferred embodiment of a flow regulator as is shown in FIG. 6. As mentioned above in FIG. 1, a worm gear causes the rotation of the worm wheel 14. As seen here, the worm wheel 14 is configured on the exterior surface of a first sleeve 60, the inside surface of which is configured with threads 62. A second sleeve 64, deployed inside the first sleeve is configured with corresponding threaded section 66 such that, when the first sleeve is rotated by the worm gear worm wheel configuration, the second sleeve is moved longitudinally, either up or down depending on the direction of rotation of the first sleeve. The longitudinal movement in turn varies the length of the elongated flow path 68 created by the grooves 70 and the inside surface of the second sleeve 64. The variance of flow path length serves to regulate the flow of the fluid through the elongated flow path configuration. An in-depth discussion of these principles may be found in U.S. Pat. No. 6,254,576.

It will be appreciated that the above descriptions are intended only to serve as examples, and that many other embodiments are possible within the spirit and the scope of the present invention.

What is claimed is:

1. A flow meter for achieving an accurate reading of the flow rate of a fluid, the flow meter comprising:

(a) a fluid flow path guide along which the fluid flows, said flow path guide being deployed at an angle with an upper end fixedly attached to a meter inlet and a lower end suspended above a reservoir attached to a meter outlet, said flow path guide having an initial position, said flow path guide configured so as to have a given elastic resiliency such that when bent and subsequently released said flow path guide returns to said initial position;

(b) a sensing device configured and deployed so as to generate an output which varies as a function of movements of said flow path guide; and (c) a processing unit in electronic communication with said sensing device, said processing unit configured to use said output from said sensing device to determine the flow rate.

2. The flow meter of claim 1, wherein said given elastic resiliency is inherent to the configuration of said flow path guide.

3. The flow meter of claim 1, wherein said flow path guide includes a conduit that is substantially closed along a dimension called length, said conduit being open to fluid flow at each of two ends.

4. The flow meter of claim 3, wherein said flow path guide includes a helical spring.

5. The flow meter of claim 1, wherein said given elastic resiliency is inherent to a material from which said flow path guide is fabricated.

6. The flow meter of claim 1, wherein said given elastic resiliency is inherent to a material from which an element, to which said flow path guide is attached, is fabricated.

7. The flow meter of claim 1, wherein said sensing device includes at least one magnetic sensor.

8. The flow meter of claim 1, wherein said sensing device includes an optical sensor.

9. The flow meter of claim 1, wherein at least one property that enables said sensing device to discern said movements of said flow path guide is inherent to a material from which said flow path guide is fabricated.

10. The flow meter of claim 1, wherein at least one property that enables said sensing device to discern said movements of said flow path guide is inherent to a material that is affixed to said flow path guide.

11. The flow meter of claim 1, wherein said flow path guide, said sensing device and said processor are housed in a single housing.

12. The flow meter of claim 1, wherein said flow path guide is deployed within a housing, said housing including said meter inlet and said meter outlet, and said sensing device and said processor are removably interconnected with said housing.

13. A flow metering system for accurately metering and regulating the flow rate of fluid flowing through a tube of a fluid delivery system, the flow metering system comprising:

(a) an adjustable flow regulator assembly having a regulator inlet, said flow regulator thereby receiving a flow of fluid, said flow regulator being configured so as to regulate the flow of fluid through said regulator, said regulator including an adjustment mechanism responsive to an adjustment actuator, said flow regulator further having a regulator outlet; and (b) the flow meter of claim 1 in fluid communication with said regulator;

wherein said adjustment actuator is in electronic communication with, and responsive to, said processing unit, so as to regulate said flow.

14. The flow metering system of claim 13, wherein the fluid delivery system includes a gravity fed intravenous fluid delivery system for delivery of fluid drugs to a patient.

15. The flow metering system of claim 14, wherein said flow regulator assembly includes a variable length elongated flow path.

16. The flow metering system of claim 15, wherein said adjustment mechanism is configured so as to vary length of said elongated flow path.

17. The flow metering system of claim 13, wherein said processing unit, and said adjustment actuator are included in a base housing unit.

18. The flow metering system of claim 13, wherein at least part of said flow regulator and at least part of said flow meter are included in a removable fluid flow path unit.

19. A flow metering method for accurately metering the flow rate of fluid flowing through a tube of a fluid delivery system, the flow metering method comprising:

(a) directing the flow along a fluid flow path guide, said flow path guide being deployed at an angle with an upper end fixedly attached to a meter inlet and a lower end suspended above a reservoir attached to a meter outlet, said flow path guide having an initial position, said flow path guide configured so as to have a given elastic resiliency such that when bent and subsequently released said flow path guide returns to said initial position, said bending being caused by weight from a build up of fluid at a lower end and said return of said flow path guide to said initial position occurring when a drop is released from said lower end of said flow path guide;

(b) sensing movements of said flow path guide; and (c) processing output resulting from said sensing, so as to derive fluid flow rate.

20. The flow metering method of claim 19, wherein the flow is regulated based on said processing.

21. The flow metering method of claim 20, wherein said regulating is accomplished by varying the length of a variable length elongated flow path.

22. The flow metering method of claim 21, wherein said varying is accomplished by activation of an adjustment actuator.

23. The flow metering method of claim 22, wherein said activation includes activation of an electric-motor-driven gear assembly.

24. The flow metering method of claim 20, wherein said regulation maintains a predetermined flow rate.

25. The flow metering method of claim 20, wherein said regulation changes the flow rate according to a predefined program.

* * * * *

UNITED STATES PATENT AND TRADEMARK OFFICE
CERTIFICATE OF CORRECTION

PATENT NO. : 6,679,865 B2 Page 1 of 1
DATED : January 20, 2004
INVENTOR(S) : Shekalim It is certified that error appears in the above-identified patent and that said Letters Patent is hereby corrected as shown below:

<u>Title page,</u>
Item [73], Assignee, "Nedrip Ltd" should be -- Medrip Ltd --

Signed and Sealed this

Twenty-second Day of June, 2004

JON W. DUDAS
*Acting Director of the United States Patent and Trademark Office*